United States Patent [19]

Sioshansi et al.

[11] Patent Number: 5,152,795
[45] Date of Patent: Oct. 6, 1992

[54] SURGICAL IMPLANTS AND METHOD

[75] Inventors: Piran Sioshansi, Bedford; Richard W. Oliver, Acton, both of Mass.

[73] Assignee: Spire Corporation, Bedford, Mass.

[21] Appl. No.: 819,348

[22] Filed: Jan. 9, 1992

Related U.S. Application Data

[63] Continuation-in-part of Ser. No. 514,503, Apr. 15, 1990.

[51] Int. Cl.$^5$ .............................................. A61F 2/28
[52] U.S. Cl. ...................................... 623/16; 623/22; 623/23; 623/66; 423/191
[58] Field of Search ........................ 623/16, 23, 66, 22

[56] References Cited

U.S. PATENT DOCUMENTS

| | | |
|---|---|---|
| 3,900,636 | 8/1975 | Curry et al. |
| 3,925,116 | 12/1975 | Engel |
| 4,465,524 | 8/1984 | Dearnaley et al. |
| 4,490,190 | 12/1984 | Speri |
| 4,568,396 | 2/1986 | Vardiman |
| 4,693,760 | 9/1987 | Sioshansi |
| 5,002,580 | 3/1991 | Noble et al. |

FOREIGN PATENT DOCUMENTS 2154450  9/1985  United Kingdom.

OTHER PUBLICATIONS

M. S. Dresselhaus et al., "Ion Implantation of Polymers" Mat. Res. So. Symp. Proc., vol. 27 (1984), pp. 413-422.
W. C. Oliver et al., "The Wear Behavior of Nitrogen-Implanted Metals" Metallurgical Transactions, A15(1984), pp. 2221-2229.
P. Sioshansi et al., "Wear Improvement of Surgical Titanium Alloys by Ion Implantation", J. Vac. Sci. Tech. A 3(6), Nov./Dec. 1985 pp. 2670-2674.
R. G. Vardiman, "Wear Improvement in Ti-6Al-4V By Ion Implantation" Naval Research Laboratory.
J. M. Williams et al., "Improvement in Wear Performance of Surgical Ti-GAl-4V Alloy by Ion Implantation of Nitrogen or Carbon", U.S. Department of Energy Jun. (1985) pp. 1-10.
J. M. Williams et al., "Effect on N-Implantation on the Corrosive-Wear Properties of Surgical Ti-6Al-4V Alloy", Mat. Res. Soc. Symposium Proc. vol. 27 (1984) pp. 735-740.

Primary Examiner—David Isabella
Assistant Examiner—Debra S. Brittingham
Attorney, Agent, or Firm—Morse, Altman, Dacey & Benson

[57] ABSTRACT

An improved surgical implant, including dental implants, formed of Ti and its alloys and a process of its manufacture are disclosed. The improved surgical implant is designed to withstand fretting wear and abrasion occasioned by vibrating micromotion of the implant against the surrounding bone structure. Such micromotion has caused undesirable blackening in the surrounding tissue and has required premature replacement of the implant.

8 Claims, 5 Drawing Sheets

SURGICAL IMPLANTS AND METHOD

This is a continuation-in-part (C.I.P.) application of pending application Ser. No. 07/514,503 filed Apr. 15, 1990, of Piran Sioshansi and Richard Oliver, entitled "Surgical Implants and Method."

BACKGROUND OF THE INVENTION

1. Field of the Invention

The present invention relates generally to surgical implants and, more particularly, to surgical implants of the modular type and formed of titanium and its alloys, and a process of improving their desirable characteristics by ion implanting the same.

2. The Prior Art

Titanium-based alloys have come to the fore of late in replacing cobalt-based alloys that had been traditionally used as surgical implants. A number of reasons are responsible for the switch to titanium-based alloys. These include: excellent tensile strength, high fatigue strength, low density, high corrosion resistance, substantial ductility, a low modulus of elasticity compatible with bone structure that facilitates good adhesion thereto and, most importantly, excellent biocompatibility. One questionable property of titanium-based alloys has proven to be their wear resistance. The wear performance of surgical implants made from titanium-based alloys already has been improved upon by ion implantation, in particular by implantation of carbon and nitrogen ions directly into the surface of the surgical implants. See "Ion Beam Modification of Materials for Industry," *Thin Solid Films*, 118 (1984) 61-71; "The Wear Behavior of Nitrogen-Implanted Metals," *Metallurgical Transactions. A* 15 (1984), 2221-2229; and "Wear improvement of surgical titanium alloys by ion implantation;" *J. Vac. Sci. Tech.* A3 (6) November/December 1985, 2670-2674. See also U.S. Pat. No. 4,693,760 granted on Sep. 15, 1987 to Piran Sioshansi, one of the co-inventors herein, and assigned to a common assignee, Spire Corporation of Bedford, Mass., the disclosure of which is incorporated herein by reference.

Titanium and its alloys are thus the most widely used alloys for securing surgical and dental implants against bone. Initially, most if not all surgical implants were secured to bone using polymethylmethacrylate (PMMA) cement for such implant to be considered as properly secured in place. When using PMMA cement, there is very little if any movement of the implant and there is but minimal contact thereof with the adjacent bone structure. In implants that are loosened over time however, there develops a micromotion between the implant and the bone or between the implant and the cement interface. Once such micromotion i.e., vibration, has developed, blackened tissue has been observed in the affected area. Micromotion of course also is present in cementless fixation of implants. Cementless fixation relies on securing the implant in and to the surrounding bone structure with frictional contact, with or without the aid of auxiliary fixation devices implanted adjacent to and concurrently with the surgical implant. The observed blackened tissue is caused by fretting wear and abrasion of the titanium alloy against the surrounding bone structure. This fretting wear and resulting blackening of tissue is and remains a vexing problem in bone and dental surgery that must be addressed and hopefully solved if present day fixation methods for such implants are to receive favorable widespread acceptance.

SUMMARY OF THE INVENTION

It is a principal object of the present invention to overcome the above disadvantages by providing an improved surgical implant made of titanium and its alloys and a process of making the same.

More specifically, it is an object of the present invention to provide a surgical implant, such as a bone or dental implant, comprising an implant formed of Ti and its alloys and including a bone fixation portion and an articulating-surface or crown fixation portion, with the bone fixation portion possessing a modulus of elasticity akin to that of bone, with the bone fixation portion of the implant being ion implanted with one of a group consisting of $N^+$, $N_2^+$, $C^+$, $Ti^+$ and $O^+$. The implant preferably is of the modular type and is one of a group including prostheses for artificial hips, knees, shoulders, elbows, fingers and toes, as well as any and all types of dental implants, including endosteal blade and cylindrical implants. Where the bone fixation portion is a femoral hip stem, the stem preferably tapers at an angle of about 2° toward its tip. Preferably, a member formed with an axial opening is designed to fit about the stem, and the axial opening of the member is tapered substantially to parallel the taper of the hip stem. Where the bone fixation portion is an endosteal blade implant, its stem preferably also tapers at an angle of from about 2° to about 4° toward its tip. Where the bone fixation portion is a cylindrical dental implant, its stem is either formed as a threaded cylinder or is of a hollow perforated design, with a partially threaded exterior. Preferably, the ion implantation is effected with an ion beam possessing an energy between about 20 keV and about 360 keV, a current density between about 0.1 and about 100 uA/cm$^2$, and a dose between about $5 \times 10^{16}$ and about $5 \times 10^{16}$ and about $3 \times 10^{18}$ ions/cm$^2$.

The ion implantation is designed to create a surface region of the ion implanted surfaces that is characterized by improved resistance to chemical attack and a surface region with a microhardness of at least about 500 knoop for a 2 grams load. Preferably, the surgical implant and the member are formed of one of a group consisting of commercially pure titanium and Ti-6A1-4V.

The process of forming an improved surgical implant according to the invention essentially includes forming an implant of Ti and its alloys and having a bone fixation portion and an articulating-surface portion, and where the implant is a femoral hip stem, a member with an axial opening designed to fit about a part of the bone fixation portion, exposing all titanium or aluminum fixtures and shields mounted within an implant chamber prior to each ion implantation to an ion beam so as to cleanse them of surface contamination and to form a surface layer thereon having a sputtering coefficient lower than that of titanium or aluminum, creating a vacuum within the implant chamber of about $3 \times 10^{-6}$ torr, introducing the implant and the member into the implant chamber to be secured therein by the cleansed and surface layer coated titanium or aluminum fixtures, and exposing the bone fixation portion of the implant and the outer surface of the member to a direct line of the ion beam, with the ion beam having an ion beam power density on the surface of the implant and the member not exceeding about 100 uA/cm$^2$ at 360 kV, i.e. 36 watts/cm$^2$, the ion beam incorporating one of a group of elemental species consisting of nitrogen, carbon, and oxygen, exposing the bone fixation portion of the implant and the outer surface of the member to the ion beam for a period of about five to fifty hours, with an ion beam particle energy from about 20 keV to about 360 keV so as to implant a dose of about $5 \times 10^{17}$ ions/cm$^2$, and wherein the ion beam current density is between about 0.1 and about 100 uA/cm$^2$.

Other objects of the present invention will in part be obvious and will in part appear hereinafter.

The invention accordingly comprises the surgical implant of the present disclosure, its components, parts and their interrelationships, and the method of making the same, the scope of the which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF PREFERRED EMBODIMENTS

In general, the present invention pertains to a surgical implant of the modular type and formed of titanium and its alloys that is designed effectively to withstand fretting wear and abrasion that may be occasioned by micromotion between the implant and adjacent bone structure and/or between two or more parts of a modular implant, and a preferred process of making the same.

Recently, titanium-based alloys have come to be preferred for use as surgical implants in lieu of cobalt-based alloys. Advantageous features of titanium-based alloys which make them preferable include excellent tensile strength, high fatigue strength, low density, high corrosion resistance, substantial ductility, a low modulus of elasticity compatible with bone structure that facilitates good adhesion between the bone structure and the alloy and, most importantly, excellent biocompatibility. Titanium and its alloys are strong, light metals that are easily malleable when heated and are ductile, particularly pure titanium. For surgical implantations, the titanium-based alloy, Ti-6Al-4V, has become the most widely used and accepted. Only one undesirable feature of titanium-based alloys has manifested itself over the years, and that has proven to be their poor wear performance.

Such poor wear performance most dramatically has manifested itself in implanted devices that become loose over time. In such loosened implants, either before or after the loosening, micromotion (i.e., vibrating motion) between the implant and the surrounding bone structure is present. Such micromotion of implant against bone subjects the implant to fretting wear and abrasion and blackens the tissue in the affected area.

Figure 1:
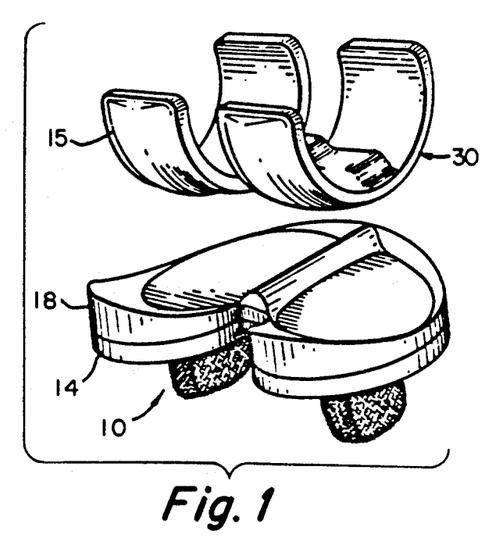
FIG. 1 is a perspective view of an artificial knee joint prosthesis made partly of titanium and its alloys and treated according to a previous process.
Figure 3:
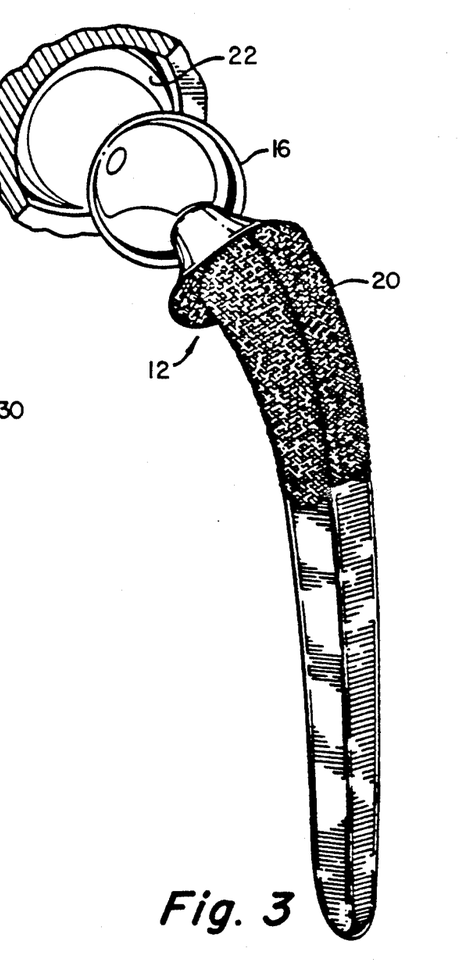
FIG. 3 is a perspective view of an artificial hip-joint prosthesis made partly of titanium and its alloys and treated according to the previous process.

In FIGS. 1 and 3 are illustrated artificial prosthesis for a knee joint 10 in the former and for a hip joint 12 in the latter. Each prosthesis 10 and 12 comprises at least one element formed of metal and a complementary mating element formed of plastic. The knee joint prosthesis 10 thus is formed of two metal parts 14 and 15, separated by a plastic part 18. The parts 14 and 15 preferably are formed of a titanium alloy, such as the surgical Ti-6Al-4V alloy. The plastic part 18 on the other hand is preferably formed of ultrahigh molecular weight polyethylene (UHMWPE). In like fashion, the hip joint prosthesis 12 is formed of a metal part 20 having a hemispherical ball portion 16, preferably formed of surgical Ti-6Al-4V alloy, and a plastic part 22, also preferably formed of UHMWPE. It is understood that the metal part 20 is placed into the femur, either by a cemented or cementless process. The low elastic modulus feature of the surgical Ti-6Al-4V alloy contributes significantly to improved load sharing in the alloy-bone or alloy-cement-bone composite of the upper femur. During walking, the alloy ball portion 16 works against the UHMWPE cup part 22. In like fashion, the metal part 15 of the knee joint prosthesis 10 works against the UHMWPE part 18 during walking. The conditions of loading, sliding velocity and body chemistry that obtain in the respective knee and hip prosthesis 10 and 12 are such as tending to produce corrosion, wear and a combination thereof in the titanium alloy and/or the UHMWPE component. In addition, the implants tend to become loose within the surrounding bone structure. Such looseness may be caused by micromotion between the implant and the bone, or the vibrating micromotion may be the result of the loosening.

The above-mentioned U.S. Pat. No. 4,693,760 addressed an undesirable by-product of ion implantation, namely surface discoloration in the ion-implanted areas. There, ion implantation was directed at improving wear performance of the cooperating parts, such as the alloy ball portion 16 working against the plastic cup part 22. Little if any attention has been directed at fretting wear and abrasion of the metallic implant against the surrounding bone structure or of one part of the metallic implant against an adjacent metallic part. Perhaps this is so since this vibrating micromotion between the implant and the bone or between parts of the implant has not been appreciated or even recognized. The blackened tissue found in the affected area has caused a study of this phenomenon. As a consequence of the study, the theory of "micromotion" was born. Micromotion is the undesirable fretting wear and abrasion of metallic implant against bone that is being addressed herein.

Figure 2:
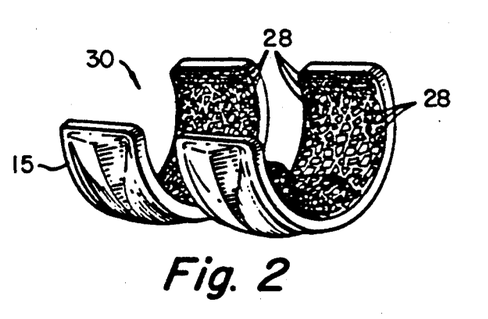
FIG. 2 is a view of a titanium alloy part of an artificial knee joint prosthesis, like the one shown in FIG. 1, but not treated according to the previous process.
Figure 4:
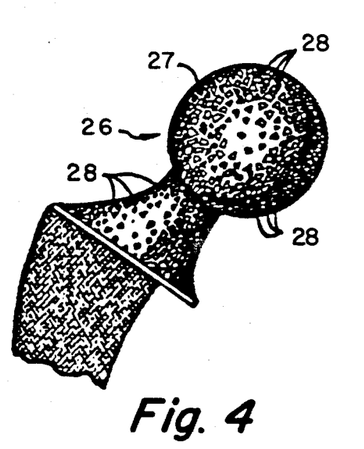
FIG. 4 is a fragmentary view of a titanium alloy component of an artificial hip-joint prosthesis like the one shown in FIG. 3, but not treated according to the previous process.

Also as mentioned, the ion implantation of the metallic parts 15 and 20 may cause surface discoloration of the parts, which make them aesthetically less than desirable both to orthopaedic surgeons and their patients slated for prosthetic implants. FIGS. 2 and 4 illustrate the problem that the process of the previous invention was designed to prevent. FIG. 2 is a view of a part 24 formed of a titanium alloy, such Ti-6Al-4V alloy, which part 24 has been ion as surgical Ti-6Al-4V alloy, which part 24 has been ion implanted with nitrogen ions, producing a concentration of about 20 at. % N to a depth of about 100 nm below the part's 24 surface, as required for improving its wear performance. FIG. 4 is a fragmentary view of a ball part 26 formed of a titanium alloy, such as surgical Ti-6Al-4V alloy, which part 26 also has been ion implanted with nitrogen ion so as to produce a concentration of about 20 at. % N to a depth of about 100 nm below its surface, as required for improving its wear performance. The surfaces 25 and 27 of both parts 15 and 26 exhibit unwanted discolorations 28. For the most part, these discolorations 28 are goldish-yellow or bluish-yellow and, like tarnishing of the metal, appear at certain locations.

Figure 5:
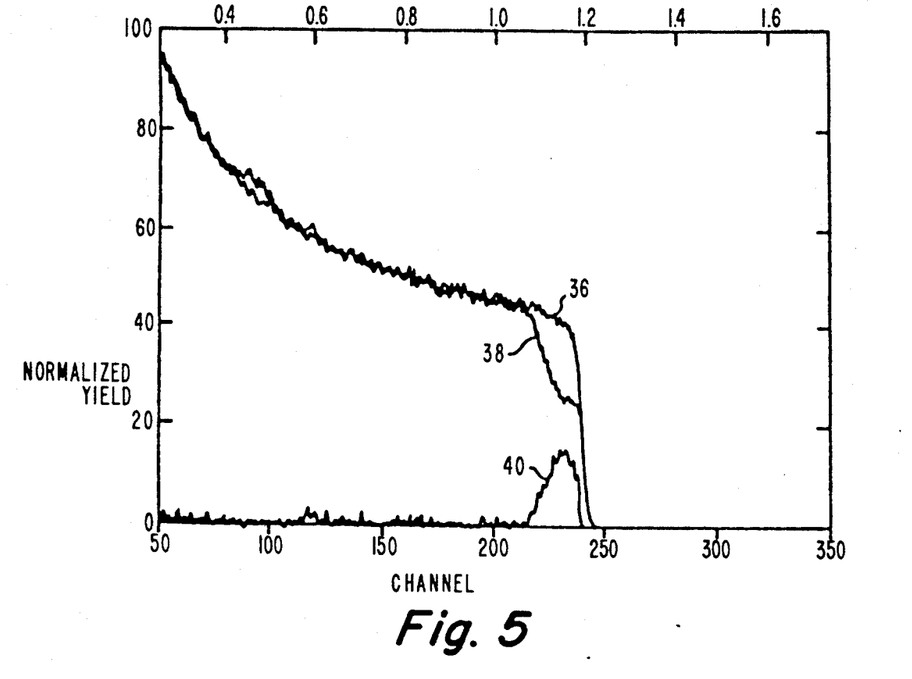
FIG. 5 depicts measurement curves helpful in understanding the previous process.

In FIG. 5 are depicted RBS measurement curves of an unimplanted sample 36 versus an implanted sample 38 formed of titanium. The sample 38 implanted with nitrogen ion has been implanted with a dose of at least about $2 \times 10^{17}$ nitrogen ions/cm$^2$ and, preferably with a dose of about $3 \times 10^{17}$ nitrogen ions/cm$^2$. The measured data show that the implanted sample 38 has a high concentration of nitrogen and oxygen on its surface (titanium oxynitride), as indicated by the curve 40. These titanium oxynitride compounds on the surfaces of the workpieces 24 and 26 are mainly responsible for the discolorations 28 thereon.

The process of the invention, producing orthopaedic implants formed of titanium and its alloys that are capable to withstand fretting wear and abrasion against bone and/or fretting wear and abrasion of one metallic implant part against another, is preferably carried out in a suitable implant chamber 44 of a specially designed endstation 46 of a suitable high current ion implanter, such as a Varian-Extrion 200 kV implanter, an Eaton-Nova implanter or a like instrument. The endstation 46 is illustrated in FIG. 6.

Within the implantation chamber 44, a suitable fixture 48 is mounted on a base 50 designed for rotating and cooling a titanium or aluminum base plate 52. On the base plate 52 are mounted a plurality of appropriately shaped workpiece holders 54, also made of titanium. These workpiece holders 54 are designed to hold securely a plurality of workpieces 58 and directly expose these workpieces 58 to an incoming ion beam 56. The illustrated workpieces 58 are the femoral components, one of which is illustrated in FIGS. 8-14. It is to be understood that the shape of the particular workpiece holders secured to the base plate 52 will depend upon the shape of the particular workpieces worked on at that time. In FIG. 7 is illustrated another workpiece, a member 59 also made of titanium or aluminum alloy and secured to one of the workpiece holders 54. Such securing of member 59 to the workpiece holder 54 preferably is effected with the aid of a shaft 70 notably mounted within holder 54 and rotatable by means of a suitable motor 72. As will be noted here and in FIGS. 8 and 10, member 59 is essentially of cylindrical shape and is formed with an axial opening 74. Preferably, the axial opening 74 is tapered to follow the taper of the stem portion 76 so as to center the hip stem within the femoral cavity, please observe FIG. 8. The free end of the mounting shaft 70 is provided with means 79 frictionally to engage, and thus secure, the tapered axial opening 74 of member 59 during its ion implantation by the ion beam 56.

Figures 6, 7:
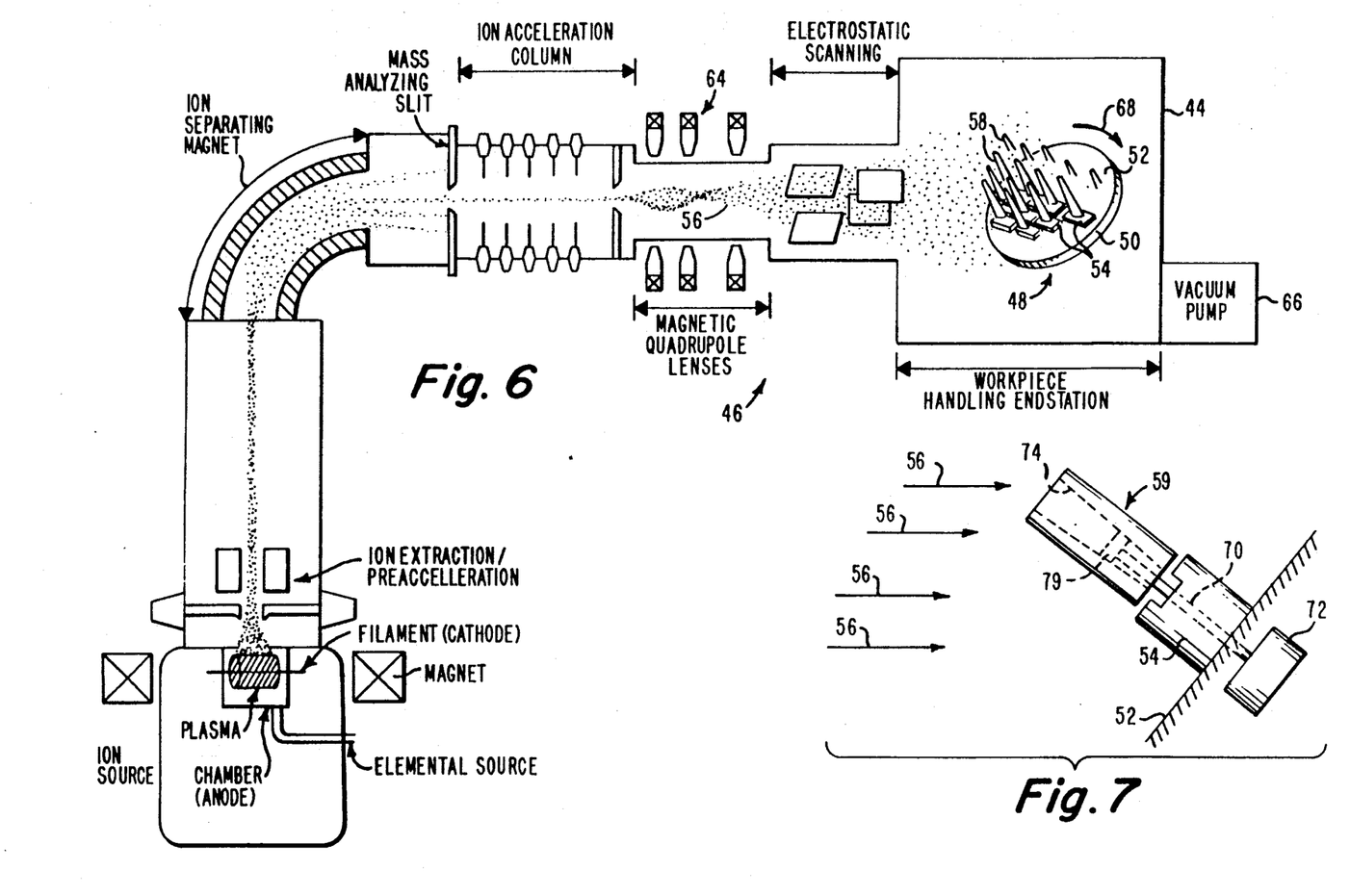
FIG. 6 is a schematic view of an ion implanter useful in carrying out the process of the invention.
FIG. 7 is a side elevation, partly in section and on an enlarged scale, of a workpiece exposed to the process of the invention according to FIG. 6.

As evident from viewing FIG. 7, the fixture 48 is so designed as to expose, at one time or another, all surfaces of the workpieces directly to the ion beam 56. Preferably and in order to achieve this, the workpieces 58 and 59 are mounted normal to the base plate 52. Thus, not only is the base plate 52 rotatable, but in addition, when the shape of the particular workpiece so requires, the workpiece 59 itself also is mounted for rotation about its longitudinal axis by a second means 72, whose rotation is independent of that of the base plate 52.

Figure 16:
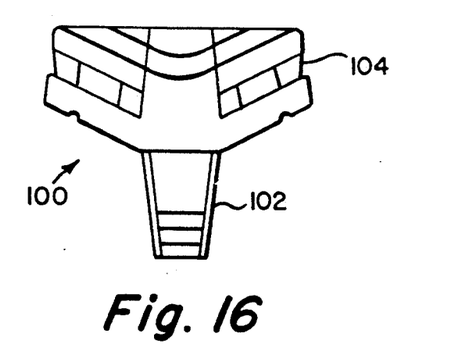
FIG. 16 is a view, on an enlarged scale, of a representative endosteal dental blade implant made according to and incorporating the present invention.
Figure 17:
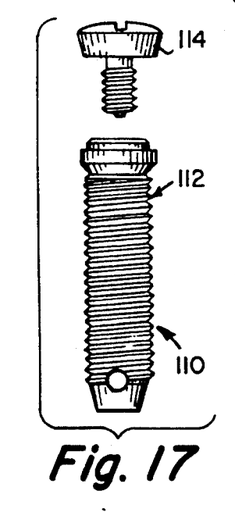
FIG. 17 is a side elevation, on an enlarged scale, of a representative dental implant of threaded cylinder design incorporating the invention.
Figure 18:
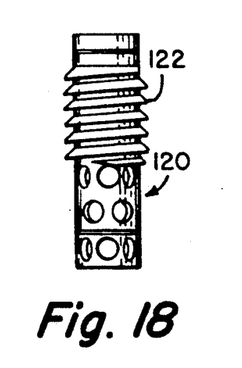
FIG. 18 is a side elevation, on an enlarged scale, of a representative dental implant of a hollow perforated design, with a partially threaded exterior, and incorporating the present invention.

In FIGS. 16-18, there is illustrated, on an enlarged scale, a representative endosteal dental blade implant 100, a representative cylindrical endosteal dental implant 110, and a representative hollow perforated endosteal dental implant 120, respectively. The dental implant 100 is shown essentially comprising a stem 102 designed to be implanted into the jawbone of a patient and a header 104, designed to have a crown (not shown) fitted thereto. The dental implant 110 essentially comprises a threaded, for the most part solid cylindrical stem 112 serving as the bone fixation portion, and a head screw 114 serving as the crown fixation portion. The dental implant 120, as illustrated, comprises a hollow, partially perforated cylinder, also featuring an externally-threaded part 122. A crown fixation portion, not shown, which may be like the head screw 114, serves as the crown fixation portion, as known. Dental implants, specifically their bone fixation portion, i.e., their stem 102, when implanted into the jawbone, are exposed to essentially identical wear condition as implanted hip stems of the press-fitted type, that is where no cement is used. These conditions include fretting wear and abrasion of the metallic implant part against the surrounding bone structure. Dental implants, as a consequence, experience similar blackening of the surrounding tissue. Patient concern is, however, now heightened due to the fact that the blackening occurs in the patient's mouth and is readily observable by the patient. The dental implants, as illustrated by the herein depicted endosteal dental blade implant 100, the cylindrical endosteal dental implant 110 and the hollow perforated dental implant 20, are subjected to the same ion implantation procedure as are the other workpieces 58 described above.

In the practice of the process of the invention, it is important that first all titanium or aluminum fixtures 48 and shields be conditioned or seasoned by being exposed to a full ion implantation dose before performing any ion implantation on titanium alloy parts within the implantation chamber 44. Such a full ion implantation dose preferably is about $3 \times 10^{17}$ ions/cm$^2$ at the surfaces of the titanium or aluminum fixtures and shields, and extending about 100 nm below those surfaces. Such a dose preferably is effected with the ion beam 56 applied to the surfaces for a period of about three and a half hours, with an ion beam particle energy from about 10 keV to about 200 keV. The ion beam 56 preferably incorporates one of a group of elemental species, including nitrogen, carbon, titanium, argon and other noble gases.

The conditioning or seasoning of the surfaces of all titanium or aluminum fixtures and shields within the implantation chamber 44 achieves two important functions: first it serves to remove any surface contamination and titanium compounds that may be present on the surfaces of these titanium fixtures and shields and, second it serves to form an appropriate surface layer, such as titanium nitride (TiN) or aluminum oxide (Al$_2$O$_3$), if nitrogen was the elemental species of the ion beam 56. The composition of this surface layer will, of course, depend which one of the elemental species, mentioned above, is incorporated in the ion beam 56. This newly formed surface layer, such as the titanium nitride (TiN) or aluminum oxide (Al$_2$O$_3$) layer, possesses a considerably lower sputtering coefficient, i.e., between about 0.06 and 0.09 at 50 keV for N+ than does pure titanium, whose sputtering coefficient is about 0.3 for 50 keV N+. It will be recalled that the titanium or aluminum fixtures 48 and shields 60 within the implantation chamber 44 are formed of pure titanium or aluminum. As stated, it is the sputtering of titanium compounds during the ion implantation of the parts 15 and 20 which is one of the causes of the discolorations 28. The seasoning of these pure titanium or aluminum fixtures 48 and shields 60 thus effectively removes this source of potential discoloration, i.e., any sputtering of titanium or aluminum compounds from those fixtures 48 and shields 60 onto the parts 15 and 20, during their ion implantation.

The next step of the process of the invention involves the creation of a proper vacuum environment within the implantation chamber 44. For, it is an improper vacuum environment within the implantation chamber 44 during the ion implantation of the parts 15 and 20 which is another cause of the discoloration 28. To this end, a vacuum within the implant chamber 44 must be created which is less than about $5 \times 10^{-6}$ and preferably is about $1 \times 10^{-6}$ torr, averaged during the ion implantation period of the parts 15 and 20. With the proper vacuum established within the implant chamber 44, with the aid of a suitable vacuum pump 66, a plurality of the workpieces 58 or 59 are introduced within the chamber 44. Preferably, the vacuum pump 66 should be of an oil-free type so as to avoid the possibility of introducing surface contamination onto the part to be ion implanted. The actual sequence of the two steps preferably is reversed, i.e., the workpieces 58 first are introduced into the chamber 44 and mounted therein in the fixtures 48, followed by the pump-down of the proper vacuum therein, it being of importance only that during the ion implantation step itself the proper average vacuum prevails, as above specified.

With the titanium and its alloy workpieces 58 secured in the fixtures 48 within the chamber 44, the workpieces 58, in particular their respective surfaces, are exposed to a direct line of the incoming ion beam 56. In order to achieve such a direct line, the fixture 48 is caused to rotate on its base 50 by motors not shown, as indicated by an arrow 68. The sputtering of titanium compounds occurs at the surfaces of the workpieces 58 from their exposed to their unexposed areas. Careful attention must also be paid to having the proper ion beam power density acting on the surfaces of the workpieces 58. For, if the ion beam power density is too high in certain areas, localized heating may well occur, which in turn will further contribute to causing the discolorations 28. This ion beam power density acting on the surfaces of the workpieces cannot exceed about 6.0 watt/cm$^2$ and preferably is about 1.0 watt/cm$^2$. Consequently, the peak ion beam power density of an 80 keV beam should not exceed about twelve microamperes per square centimeter.

The control of the ion beam power density can be achieved in a number of ways. Preferably, and as herein illustrated, this low power ion beam current density is effected by expanding the spot size of the incoming ion beam 56 (observe FIG. 6) by a magnetic quadruple or an electro-static lens system 64. The surfaces of the workpieces 58, now secured in the fixture 48 within the implant chamber 44, are then exposed to the incoming ion beam 56, properly modified, if need be, by the lens system 64, for a period from about five hours to about fifty hours, with a preferred ion beam particle energy from about 20 keV, to about 360 keV, so as to implant a dose of about $5 \times 10^{17}$ ions/cm$^2$ and wherein the ion beam current density is between about 0.1 and about 100 uA/cm$^2$.

The workpiece 58 illustrated in FIGS. 6–15 and the representative endosteal dental blade implant 100 illustrated in FIG. 16 are respectively formed of Ti and its alloys. The workpiece 58 is of the modular type and includes a bone-fixation portion 80 and an articulating-surface portion 82 press-fitted against the bone-fixation portion 80. The outer size of the articulating surface portion 82 varies, allowing the surgeon easily to accomodate for differing patient requirements by selecting the particular outer dimension thereof for a particular patient. The dental implant 100 is formed of the stem 102, which functions as the bone-fixation part. Preferably, these bone-fixation parts 80 and 102 are designed so as to possess a modulus of elasticity of about $15(\pm 1) \times 10^6$ p.s.i., which is closely akin to that of human bone 90, whose modulus of elasticity is about $10-30 \times 10^5$ p.s.i.

As mentioned, and unlike the hip-joint prosthesis 12 of FIG. 3, the bone fixation portion 80 of the workpiece 58 is thinner than that of prosthesis 12 and is tapered along its axial length toward its distal tip 84. This bone-fixation portion 80, i.e., the femoral hip stem, preferably has a length 86 of about 25 cm from an extraction hole 88 to its distal tip 84, and a preferred thickness of about one to two cm about midway therebetween. Hole 88 is an extraction hole used for removing, if need be, the bone-fixation portion 80 from the intermedullary canal 78. Further, the hip stem also tapers at a preferred angle of about one to two degrees at this midway section toward its tip 84. It will be noted that the axial opening 74 of the centering sleeve member 59 also tapers at substantially the same angle so as closely to parallel the taper of the bone-fixation portion 80.

Preferably, both the member 59 and the workpiece 58 are formed of the same Ti and its alloy so that they can be compatible as much as possible. The entire outside surface of the bone-fixation portion 80 and the entire outside surface of the member 59 are ion implanted with an ion beam possessing an energy between about 20 keV and about 360 keV, a current density between about 0.1 and about 100 uA/cm$^2$, and a dose between about $5 \times 10^{16}$ and about $3 \times 10^{18}$ ions/cm$^2$. Preferably, the ion implantation creates a surface region of the ion implanted surfaces characterized by improved resistance to chemical attack and a surface region with a microhardness of at least about 500 Knoop. Knoop hardness is determined by the Knoop indentation test in which a diamond indenter is used to penetrate the surface. Preferably, the implant 58 and the member 59 are formed of one of a group consisting of commercially pure titanium and Ti-6Al-4V.

Figures 8, 9, 10:
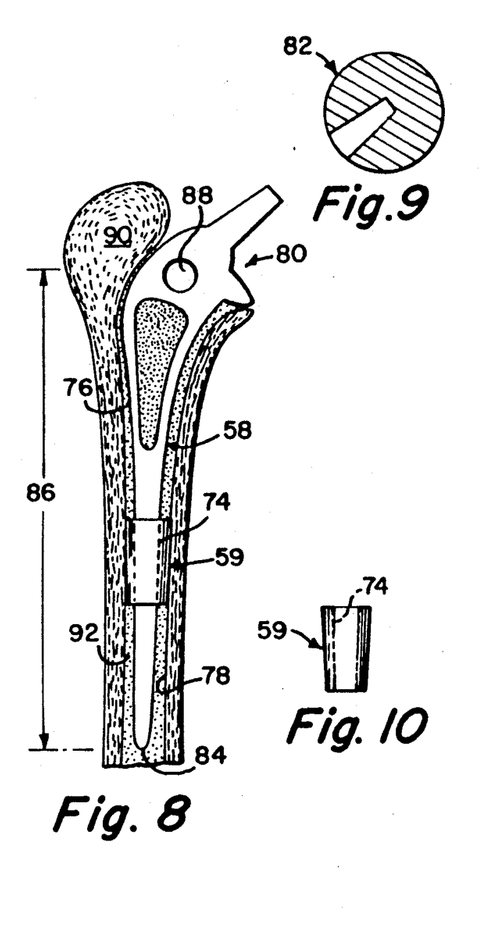
FIG. 8 is a schematic cross section of an artificial hip-joint prosthesis with a sleeve component used for centering a hip stem within a femoral cavity and made according to and incorporating the present invention.
FIG. 9 is a schematic of a component part of the hip-joint prosthesis illustrated in FIG. 8.
FIG. 10 is a view of the sleeve component part of the hip-joint prosthesis illustrated in FIG. 8.

As may be observed in FIG. 8, the bone-fixation portion 80 of the implant workpiece 58 is positioned within the intermedullary canal 78, which is wider than the tapering bone-fixation portion 80 of the implant workpiece 58. So as to securely center and fix the implant workpiece 58 within this canal 78, the centering sleeve member 59 is used to fill the void between the femoral stem and the canal 78. The fixation of these two parts 58 and 59 to the bone can be effected with or without the use of cement 92, such as polymethyl methacrylate (PMMA) cement, at the discretion of the surgeon. If cement 92 is used, it will occupy the free space between the hip stem 58 and the intermedullary canal 78, both above and below the member 59, as shown. The articulating-surface portion 82 is then secured to the stem 80, and the artificial hip joint is completed in the usual manner.

Figures 11, 12, 13:
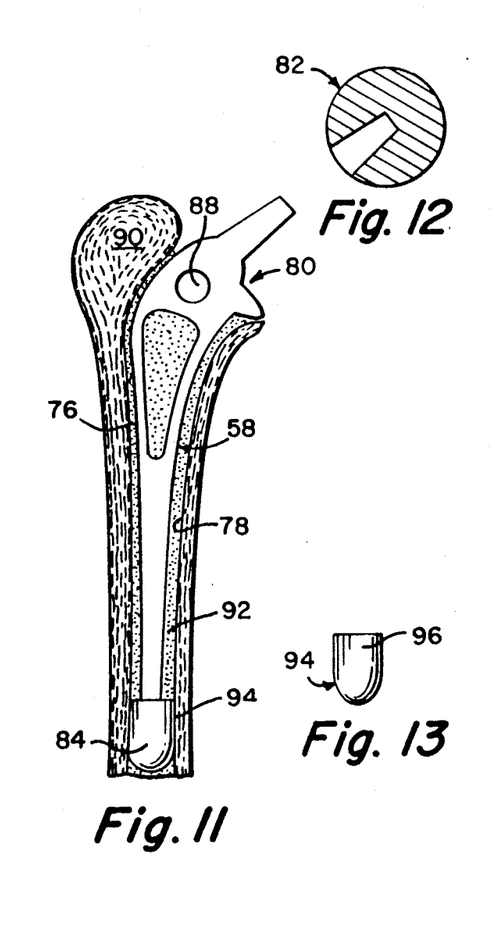
FIG. 11 is a view similar to FIG. 8 but showing a distal tip component used for centering a hip stem within a femoral cavity.
FIGS. 12 and 15 are views similar to FIG. 9.
FIG. 13 is a view similar to FIG. 10 but illustrating the distal tip component of FIG. 11.

In FIGS. 11-13, there is illustrated a different embodiment of securing the implant workpiece 58. In lieu of the centering sleeve member 59, positioned about midway between the proximal and distal parts of the hip stem 58, a distal tip member 94 is employed to center the hip stem 58. It will be noted that the distal tip member 94 is provided with a central bore 96 designed to accommodate therein the distal tip 84 of the hip stem 58. Again and at the discretion of the surgeon, the space between the hip stem 58 and the intermedullary canal 78 may be filled with PMMA cement 92, extending both above and below the member 94.

Figures 14, 15:
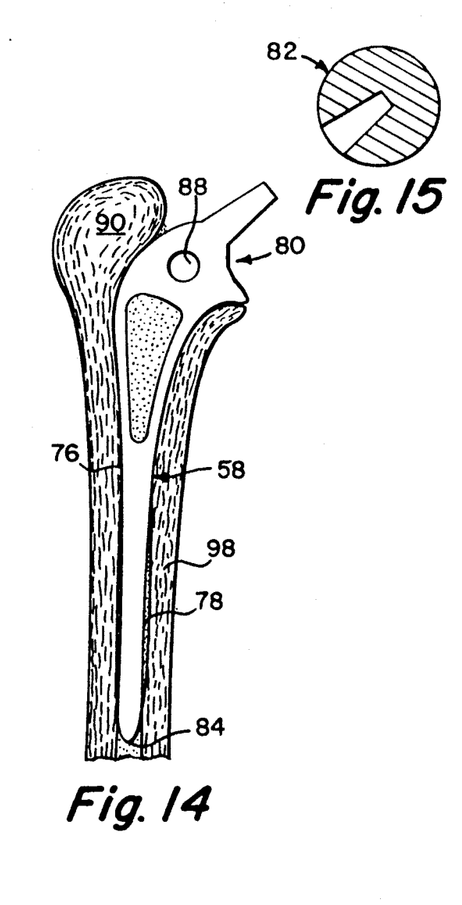
FIG. 14 is a view similar to FIGS. 8 and 11 but illustrating the press fitting of a hip stem within a femoral cavity.

In FIG. 14 is illustrated yet another embodiment of securing the implant workpiece 58, i.e., the hip stem, within the femoral cavity, i.e., the intermedullary canal 78, namely by being press-fitted therein. In press-fitting an implant within a bone cavity, no cement is used around the implant and within bone cavity. Some surgeons in the field, including the dental field, are concerned that the cement layer surrounding the implant inhibits further bone growth about the implanted part. Some surgeons even fear that the presence of PMMA cement might actually cause bone tissue surrounding the implant to die. Lately, especially in dental practice, cementless fitting closely against the surrounding bone structure is preferred. In either event, loosening of the implant will occur over time. When loosening of an implant occurs, revision surgery is the only remedy to remove the old device and install a new one. Revision surgery entails the scraping out the cement, in addition to removing the old device, followed by preparing the femur for the new implant. This requires the removal of even more bone tissue, a further undesirable consequence. When revision surgery on a cementless implant is required, at least the loss of surrounding bone tissue is not as great as with a cemented implant. As may be noted in FIG. 14, the intermedullary canal 78 closely follows the taper 76 of the hip stem 58, with a wider bone structure 98 remaining in the femur, following implant.

The ion implantation of the hip stem 58, the fixation members 59, 94 and 114, and of the stems 102 and 112 of the endosteal dental blade implant 100 and the cylindrical dental implant 110, as well as the hollow cylindrical dental implant 120 and any crown fixation member thereof assure that the fretting wear and abrasion of those implants against the surrounding bone structure are minimized, reducing patient stress, discomfort and the need of premature repair and/or replacement of the implants.

Figure 19:
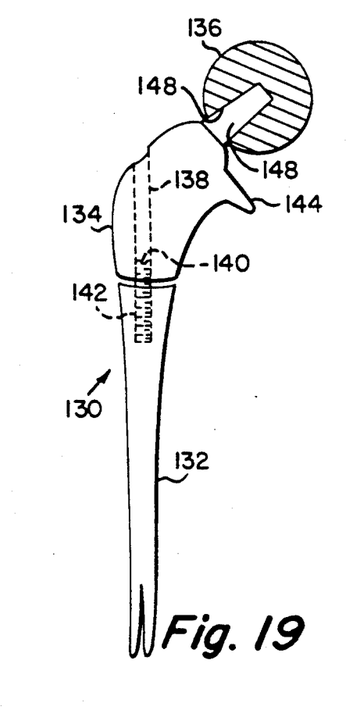
FIG. 19 is a view similar to FIG. 8 but illustrating a different artificial hip-joint prosthesis according to the invention.
Figure 20:
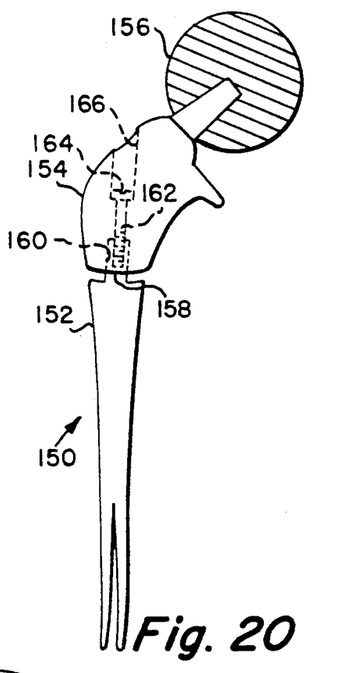
FIG. 20 is a view similar to FIG. 19 but illustrating another type of artificial hip-joint prosthesis according to the invention.
Figure 21:
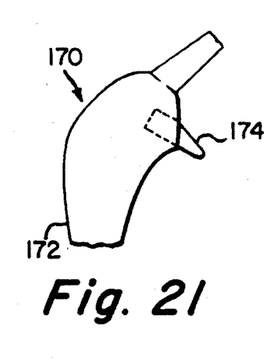
FIG. 21 is a fragmentary view of still another type of artificial hip-joint prosthesis, according to the invention.

Further surgical implants of the modular type, in addition to those illustrated in FIGS. 8-15, are shown in FIGS. 19-21.

FIG. 19 is a view similar to FIG. 8 but illustrates a modular artificial hip-joint prosthesis 130 formed of three individual and interchangeable parts. These parts comprise a stem 132, a stem-head 134 and a ball 136, each respectively secured to the other. The stem-head 134 is provided with a longitudinal bore 138 designed to accomodate a screw 140. The proximal end of the stem 132 is in turn provided with an internally threaded section 142 to receive the externally threaded portion of the of the screw 140. No matter how tightly the screw 140 is turned, when the implant 130 is in place in a walking human being, fretting wear and abrasion do occur as between the stem 132 and the stem-head 134, in addition as between the implant 130 and the surrounding bone tissue of the intramedullary canal. The stem-head 134 is furthermore provided with a tab 144 designed to rest against a part of the femur, and with a tapered mounting stem 146. The ball 136, which is designed to articulate within a plastic acetabular cup (not shown here, but one is shown in FIG. 3, as at 22), is in turn provided with a tapered mounting hole 148. The ball 136 is then press fit over the tapered mounting stem 46. Fretting wear and abrasion also occur between the interfaces of the mounting stem 146 and the mounting hole 148, as well as between the tab 144 and the adjacent bone tissue.

FIG. 20 is a view similar to FIG. 19 but illustrates another modular artificial hip-joint prosthesis 150 also formed of three individual and interchangeable parts. The parts comprise a stem 152, a stem-head 154 and a ball 156. In order to minimize undesirable micromotion between the stem 152 and its head 154, its construction features a member 158 formed integrally with the stem 152 at its proximal mating end and designed to extend into an appropriately formed channel 160 within the stem-head 154. In addition, member 160 is formed with an internally-threaded portion 162 to accomodate therein a screw 164 operatively introduced into the stem-head 54 through a bore 166. Prosthesis 150 is in all other respects identical to the one shown in FIG. 19.

In FIG. 21 is illustrated in fragmentary view and without any ball, a further modular artificial hip-joint prosthesis 70. Prosthesis 170 is formed of a single stem 172, just like those illustrated in FIGS. 8, 11 and 14. Instead of being provided with an integrally formed tab 144, as in FIG. 19, prosthesis 170 features an interchangeable press-fit tab 174, each of differing sizes, designed to fit to different bone structures. The press-fit tab 174 is accomodated within an appropriately shaped bore, as shown.

The process of the invention, and the resultant product, are intended to prevent or at least to inhibit the undesirable consequences of micromotion as between the implant and the surrounding bone tissue and the several parts of the implant working against each other, namely fretting wear and abrasion, causing premature failure of the implant, requiring premature replacement. The exposing of the implants, in particular those of their surfaces which come into contact with surrounding bone tissue or rub against each other, is designed to provide such implant surfaces with a surface region therein characterized by improved resistance to chemical attack and a surface region with a microhardness of at least about 500 Knoop for a two-gram load.

Thus it has been shown and described an improved orthopaedic implant made from titanium and its alloys and a process designed to improve their fretting wear performance against bone, which product and process satisfy the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A surgical implant comprising:
   (a) a modular implant formed of Ti and its alloys and including a tapered section and a ball section, said tapered section having an outside surface and formed of a proximal and a distal part;
   (b) said outside surface of said tapered section, including said proximal and said distal part of said implant being ion implanted with one of a group consisting of $N^+$, $N_2^+$, $C^+$, $Ti^+$, and $O^+$;
   (c) said ion implantation being effected with an ion beam possessing an energy between about 20 keV and about 360 keV, a current density between about $5 \times 10^{16}$ and about $3 \times 10^{18}$ ions/cm$^2$;
   (d) said tapered section of said implant being formed of one of a group consisting of commercially pure titanium and Ti-6Al-4V;
   (e) said tapered section of said implant tapering toward a distal tip of said distal part;
   (f) a member formed with an axial opening configured to fit about a middle part of said bone fixation portion and dimensioned for centering said implant, said member also being ion implanted with one of said group;
   (g) said axial opening of said member tapered complementary to said taper of said bone fixation portion;
   (h) said ion implantation creating a surface region of the ion implanted surfaces characterized by improved resistance to fretting, abrasion and chemical attack and a surface region with a microhardness of at least 500 Knoop for a 2 gram load.

2. The surgical implant of claim 1 wherein said implant is one of a group consisting of said tapered sections of prostheses for artificial hips, knees, shoulders, elbows, fingers, toes, and dental implants, wherein said ion implantation being effected with an ion beam possessing an ion beam power density on said outside surfaces of said bone fixation portion and of said articulating surface portion not exceeding about 6.0 watt/cm$^2$, and further including a tapered mounting stem projecting from said proximal part of said tapered section, said ball section having an articulating outside surface and an inside surface, said inside surface configured to press fit over said tapered mounting stem of said tapered section.

3. The surgical implant of claim 1 wherein said implant is a dental implant and wherein said tapered section thereof is a member designed to be press fitted into a cavity formed in the jaw bone of a patient.

4. The surgical implant of claim 1 wherein said ion implantation of said implant includes those surfaces thereof that abut against each other where said modular implant is assembled as well as those surfaces that abut against adjacent bone tissue when assembled and implanted.

5. A surgical implant comprising:
   (a) an implant formed of Ti and its alloys, said implant being a dental implant;
   (b) said dental implant comprising a bone fixation portion and a crown fixation portion;
   (c) the outside surfaces of said dental implant being ion implanted with one of a group consisting of $N^+$, $N_2^+C^+$, $Ti^+$ and $O^+$; said ion implantation being effected with an ion beam possessing an energy between about 20 keV and about 360 keV, a current density between about $5 \times 10^{16}$ and about $3 \times 10^{18}$ ions/cm$^2$;
   (d) said ion implantation creating a surface region of the ion implanted surfaces characterized by improved resistance to chemical attach and a microhardness of at least about 500 Knoop for a 2 gram load.

6. The surgical implant of claim 5 wherein said dental implant is an endosteal dental blade implant, and wherein said bone fixation portion is a stem formed with a taper away from said crown fixation portion.

7. The surgical implant of claim 5 wherein said dental implant is a cylindrical endosteal dental implant, wherein said bone fixation portion is a solid cylindrical stem provided with a threaded exterior and an internally threaded section at one end thereof, and wherein said crown fixation portion is formed as a head screw having an externally threaded section designed to be received with said internally threaded section of said stem.

8. The surgical implant of claim 5 wherein said dental implant is a hollow perforated endosteal dental implant, wherein said bone fixation portion is a hollow, partially perforated and partially externally-threaded hollow cylinder, said hollow cylinder provided at one end thereof with an internally-threaded section, and wherein said crown fixation portion is formed as a head screw having an externally-threaded section designed to be received within said internally-threaded section of said cylinder.

* * * * *